US010327320B2

(12) United States Patent
Matsushita

(10) Patent No.: US 10,327,320 B2
(45) Date of Patent: Jun. 18, 2019

(54) HIGH-FREQUENCY POWER SUPPLY FOR PLASMA AND ICP OPTICAL EMISSION SPECTROMETER USING THE SAME

(71) Applicant: SHIMADZU CORPORATION, Kyoto-shi, Kyoto (JP)

(72) Inventor: Tomoyoshi Matsushita, Kyoto (JP)

(73) Assignee: SHIMADZU CORPORATION ( * ) Notice: Subject to any disclaimer, the term of this patent is extended or adjusted under 35 U.S.C. 154(b) by 19 days.

(21) Appl. No.: 14/017,103

(22) Filed: Sep. 3, 2013

(65) Prior Publication Data

US 2014/0118735 A1 May 1, 2014

(30) Foreign Application Priority Data

Oct. 25, 2012 (JP) ................. 2012-235447

(51) Int. Cl.
H05H 1/24 (2006.01)
H05H 1/30 (2006.01)
G01N 21/73 (2006.01)

(52) U.S. Cl.
CPC .............. H05H 1/24 (2013.01); G01N 21/73 (2013.01); H05H 1/30 (2013.01)

(58) Field of Classification Search
CPC ............ G01N 21/73; H05H 1/30; H05H 1/28; H05H 1/26; H05H 1/24; H01L 23/467; H01L 23/473; H01L 23/34; H01L 23/36–38; H01L 23/46–4735
See application file for complete search history.

(56) References Cited

U.S. PATENT DOCUMENTS 3,958,883 A * 5/1976 Turner .................... 356/316
4,429,736 A * 2/1984 Turner .................... 165/61
5,361,188 A * 11/1994 Kondou et al. ............... 361/695
(Continued)

FOREIGN PATENT DOCUMENTS

CN 1263638 A 8/2000
CN 201197253 Y 2/2009
(Continued)

OTHER PUBLICATIONS

Integrated Circuit. (2015). In the Columbia Encyclopedia. New York, NY: Columbia University Press. Retrieved from http://search.credoreference.com/content/entry/columency/integrated_circuit/0.*
(Continued)

Primary Examiner — Shawn Decenzo
Assistant Examiner — Rufus L Phillips
(74) Attorney, Agent, or Firm — McDermott Will & Emery LLP

(57) ABSTRACT

In a high-frequency power supply for plasma having a housing and a high-frequency circuit substrate placed inside the housing elements for supplying a high-frequency current to a high-frequency inductive coil are mounted on the high-frequency circuit substrate, a cooling block for cooling the high-frequency circuit substrate, a fan for sending air to the elements on the high-frequency circuit substrate as wind are further provided, and fins for allowing air to flow through so that the air is cooled are formed on the surface of the cooling block. The housing is provided with an air path for supplying the air that has flown through the fins to the absorbing side of the fan.

16 Claims, 5 Drawing Sheets

(56) References Cited

U.S. PATENT DOCUMENTS

| | | | | |
|---|---|---|---|---|
| 5,901,037 | A * | 5/1999 | Hamilton | F28F 3/12 165/80.4 |
| 5,923,086 | A * | 7/1999 | Winer et al. | 257/713 |
| 5,978,218 | A * | 11/1999 | Fujimoto et al. | 361/696 |
| 5,987,893 | A * | 11/1999 | Schulz-Harder | F25B 21/02 136/204 |
| 5,995,387 | A * | 11/1999 | Takahashi | H02M 3/33523 363/21.04 |
| 6,208,510 | B1 * | 3/2001 | Trudeau | H05K 7/20609 165/80.3 |
| 2008/0253090 | A1 * | 10/2008 | Janisch | H01L 23/3677 361/709 |
| 2010/0228089 | A1 * | 9/2010 | Hoffman | A61B 1/063 600/182 |
| 2011/0284862 | A1 * | 11/2011 | Zhang | H01L 27/085 257/76 |
| 2014/0110380 | A1 * | 4/2014 | Kamath | B23K 10/00 219/121.39 |

FOREIGN PATENT DOCUMENTS

| | | |
|---|---|---|
| JP | 59-171838 A | 9/1984 |
| JP | 1-175298 A | 7/1989 |
| JP | 08-088490 A | 4/1996 |
| JP | 2001-274299 A | 10/2001 |
| JP | 2003215042 A | 7/2003 |
| JP | 2009-516905 A | 4/2009 |
| JP | 2010-187504 A | 8/2010 |
| JP | 2010-193695 A | 9/2010 |
| JP | 11-101748 A | 4/2013 |

OTHER PUBLICATIONS

Office Action Chinese Patent Application No. 201310471413.3 dated Sep. 1, 2015.

Office Action Japanese Patent Application No. 2012-235447 dated Apr. 26, 2016.

Notification of Reasons for Refusal Japanese Patent Application No. 2012-235447 dated Dec. 8, 2015 with full English translation.

* cited by examiner

HIGH-FREQUENCY POWER SUPPLY FOR PLASMA AND ICP OPTICAL EMISSION SPECTROMETER USING THE SAME

TECHNICAL FIELD

The present invention relates to a high-frequency power supply for plasma and an ICP optical emission spectrometer using the same.

BACKGROUND ART

In an ICP optical emission spectrometer, a sample is introduced into a plasma flame so as to emit light through excitation. The thus-emitted light is dispersed through a grating so as to be detected by a photodetector, and as a result, an emission spectrum is acquired. In addition, an element contained in the sample is qualitatively analyzed by the type of wavelength in the spectrum line (bright line spectrum) that appears in the emission spectrum, and furthermore, the element is quantitatively analyzed by the intensity of this bright line spectrum (see Patent Document 1).

FIG. 5 is a schematic diagram showing the structure of an example of a conventional ICP optical emission spectrometer. An ICP optical emission spectrometer 200 is provided with a plasma torch 18 for optical emission spectrometry from which a plasma flame 22 is generated, a sample gas-supplying unit 44, a plasma gas-supplying unit 41, a cooling gas-supplying unit 42, a light measuring unit 43 for detecting the emitted light, a high-frequency power supply 130 for plasma that supplies a high-frequency current I, and a computer (control unit) 150 for controlling the entirety of the ICP optical emission spectrometer 200.

The plasma torch 18 for optical emission spectrometry is provided with a sample gas tube 11 in cylindrical form, a plasma gas tube 12 in cylindrical form that covers the outer periphery of the sample gas tube 11 with a space in between, a coolant gas tube 13 in cylindrical form that covers the outer periphery of the plasma gas tube 12 with a space in between, and a high-frequency inductive coil 21 with two to three loops around the end portion of the outer periphery of the coolant gas tube 13.

The plasma gas-supplying unit 41 allows argon gas to flow in the upward direction at a relatively low speed between the outer periphery of the sample gas tube 11 and the inner periphery of the plasma gas tube 12. As a result, argon gas is jetted from the upper end portion of the flow path created between the outer periphery of the sample gas tube 11 and the inner periphery of the plasma gas tube 12. When the jetted argon gas is ionized by the electrons that have been accelerated by the high-frequency electromagnetic field created by the high-frequency inductive coil 21, argon cations and electrons are generated. The generated electrons further collide with argon so as to proliferate the ionization, and thus, a stable plasma flame 22 is generated in the upper end portion.

The cooling gas-supplying unit 42 allows the argon gas to flow in the upward direction at a relatively high speed between the outer periphery of the plasma gas tube 12 and the inner periphery of the coolant gas tube 13. As a result, argon gas is jetted from the upper end portion of the flow path created between the outer periphery of the plasma gas tube 12 and the inner periphery of the coolant gas tube 13, and the thus-jetted argon gas flows in the upward direction along the outside of the plasma flame 22 that has been generated in the upper end portion.

When a sample is analyzed, the sample and the argon gas are made to flow in the upward direction through the space surrounded by the inner periphery of the sample gas tube 11. The sample is jetted from the end portion of the sample gas tube 11 together with the argon gas so as to be introduced into the plasma flame 22. As a result, a compound included in the sample makes contact with the plasma flame 22 and is converted to an atom or is ionized so as to emit light through excitation.

The light measuring unit 43 has a housing 43a, a condenser lens 43b for introducing the light emitted from the plasma torch 18 for optical emission spectrometry into the housing 43a, a grating 43c for dispersing the emitted light, and a photodetector 43d for detecting the emission spectrum.

The computer 150 is formed of a CPU 151 and input apparatuses 52, such as a keyboard and a mouse, and carries out a qualitative analysis on an element contained in the sample on the basis of the type of wavelength of the bright light spectrum in the emission spectrum detected by the photodetector 43d, and furthermore carries out a quantitative analysis on the element on the basis of the intensity of the bright light spectrum.

The above-described ICP optical emission spectrometer 200 is provided with a high-frequency power supply 130 for plasma that supplies a high-frequency current I to the high-frequency inductive coil 21. The plasma high-frequency power supply 130 is provided with a housing 131 having openings 131a and 131b, a high-frequency circuit substrate 132 placed inside the housing 131, and a cooling fan 133 placed in proximity to the opening 131a of the housing 131.

The housing 131 is in rectangular parallelepiped form having a space inside (50 cm×20 cm×35 cm, for example) where the opening 131a is created at the bottom while the opening 131b is created at the top.

The high-frequency circuit substrate 132 consists of two substrates (30 cm×20 cm×1.6 mm, for example) made of FR4 (Flame Retardant Type 4, thermal conductivity: 0.33 W/mk) in plate form, and transistors, large-scale capacitors and amplifying circuits, which are elements for supplying a high-frequency current I to the high-frequency inductive coil 21, are mounted on the upper surface the substrates. In addition, conventional grease (thermal conductivity: 0.9 W/mk) is applied to the upper surface of the substrates. The high-frequency circuit substrate 132 is placed in the center portion inside the housing 131.

The cooling fan 133 is placed in proximity to the opening 131a in such a manner that the absorbing side is on the bottom and the exhaust side is on the top. In addition, when the fan rotates, the air is allowed to pass from the opening 131a of the housing 131 to the opening 131b of the housing 131 through the inside of the housing 131.

In the thus-formed high-frequency power supply 130 for plasma, elements on the high-frequency circuit substrate 132 emit heat when a high-frequency current I is supplied, and therefore, the cooling fan 131 is rotated so as to allow air to flow, and thus, the heat generated from the elements on the high-frequency circuit substrate 132 is radiated.

In some other ICP optical emission spectrometers, a matching box is provided between the high-frequency power supply 130 for plasma and the high-frequency inductive coil 21 so as to form a structure for reducing the waves reflected from the high-frequency inductive coil 21, and the impedance is matched by changing the capacitance by means of the matching box.

PRIOR ART DOCUMENT

Patent Document

Patent Document 1: Japanese Unexamined Patent Publication H11 (1999)-101748

SUMMARY OF THE INVENTION

Problem to Be Solved by the Invention

A number of transistors and large-scale capacitors are mounted on the upper surface of the high-frequency circuit substrate 132 in plate form in the above-described ICP optical emission spectrometer 200, which also has amplifying circuits in multiple stages, and therefore is costly and large.

In order to achieve the reduction in the size and cost, the present invention changed the control system for the high-frequency power supply from a conventional capacitance-tuning system with a fixed frequency, where a number of transistors and large-scale capacitors were mounted, to a self-oscillation system, and fabricated a power MOSFET, a compact ceramic capacitor, a pulse transformer, an L (inductor, an L-copper plate in an LC circuit) and a bypass capacitor mounted on a high-frequency circuit substrate. In the case of the self-oscillation system, it is necessary for the path through which a high-frequency current flows to be patterned as the shortest by using a power semiconductor element in order to reduce the power loss due to the inductance of the path of the high-frequency current, which leads to a reduction in the scale of the system.

In addition, the heat density (the amount of heat emissions) of each element increased, and therefore, it was determined to use a cooling block made of a metal (made of copper, for example) where cooling water (coolant) flows through the inside instead of the use of a cooling fan for allowing the air to flow. That is to say, the power MOSFETs having a very high heat density (amount of heat emission: 500 W) were cooled by the cooling block, and at the same time, compact ceramic capacitors, pulse transformers, wires, Ls (inductors) and bypass capacitors were naturally cooled with air. However, the cooling of the compact ceramic capacitors, Ls (inductors) and pulse transformers was insufficient.

Furthermore, the cooling was insufficient even when only the cooling fan for allowing air to flow was used to cool the power MOSFETs, compact ceramic capacitors, pulse transformers, wires, Ls (inductors) and bypass capacitors as a forced air cooling system.

Means for Solving Problem

The present inventor examined the cooling method for cooling the elements on the high-frequency circuit substrate. It was found that some elements mounted on the high-frequency circuit substrate were appropriate for cooling through heat conduction (power MOSFETs, wires) and other elements were inappropriate for cooling through heat conduction (compact ceramic capacitors, Ls (inductors)) depending on the structure of the part or the method for attaching the part to the substrate (the size of the area of contact with the substrate, for example). Thus, it was found that the elements that were appropriate for cooling through heat conduction were cooled by the cooling block, and at the same time, the elements that were inappropriate for cooling through heat conduction were cooled through forced air cooling where wind from the cooling fan directly hit the elements. It was also found that the air cooled by the cooling block was supplied to the absorbing side of the cooling fan.

That is to say, the high-frequency power supply for plasma according to the present invention is provided with a housing, a high-frequency circuit substrate placed inside the housing, a cooling block for cooling the high-frequency circuit substrate, and a fan for sending air to the elements on the above-described high-frequency circuit substrate. Elements for supplying a high-frequency current to a high-frequency inductive coil are mounted on the high-frequency circuit substrate of the high-frequency power supply for plasma, and the high-frequency power supply for plasma according to the present invention is characterized in that fins for allowing air to be cooled when the air flows are formed in the above-described cooling block, and an air path for allowing the air that has flown through the above-described fins to be supplied to the absorbing side of the above-described fan is provided in the above-described housing.

Effects of the Invention

As described above, in the high-frequency power supply for plasma according to the present invention, the elements mounted on the high-frequency circuit substrate can be sufficiently cooled, making it possible to continuously turn on the plasma flame.

Other Means for Solving Problem and Effects of the Invention

In the above-described high-frequency power supply for plasma according to the invention, the above-described fan and the above-described high-frequency circuit substrate may be arranged so as to face each other, and at the same time, the elements that are inappropriate for cooling by means of the above-described cooling block may be placed in the region on the above-described high-frequency circuit substrate that faces the portion to which the above-described fan exhausts air so that the air can be sent directly to these elements.

Moreover, in the above-described high-frequency power supply for plasma according to the invention, the elements that are inappropriate for cooling by means of the above-described cooling block are capacitors, pulse transformers and inductors.

In addition, in the above-described high-frequency power supply for plasma according to the invention, the inside of the above-described housing may be sealed airtight and may by provided with the above-described cooling block, the above-described fan and the above-described air path.

As described above, in the high-frequency power supply for plasma according to the present invention, dust does not enter into the housing because the inside of the housing is a sealed space, and thus, the elements on the high-frequency circuit substrate can be prevented from being broken in the case where the ICP optical emission spectrometer is used in a harsh environment, such as in an acid atmosphere or in an atmosphere that includes seawater, where dust tends to enter through an opening of the housing together with air and adhere to the elements on the high-frequency circuit substrate, which may short circuit or corrode and break the elements.

According to the present invention, the inside of the housing of the high-frequency power supply for plasma is a sealed space that is shielded from the outside air. However, the air that has been warmed by absorbing the heat from the elements passes through the fins formed in the cooling block so that the heat can be released to the cooling block and the cooled air can be supplied to the absorbing side of the fan.

In addition, in the high-frequency power supply for plasma according to the present invention, the above-described high-frequency circuit substrate may be placed on the upper surface of the above-described cooling block, and at the same time, the above-described fins may be formed on the lower surface of the above-described cooling block, and the above-described fan may be placed above the above-described high-frequency circuit substrate.

Furthermore, in the high-frequency power supply for plasma according to the present invention, a coolant path for allowing a coolant to flow through may be formed inside the above-described cooling block or a Peltier element may be attached to the above-described cooling block.

Thus, the ICP optical emission spectrometer according to the present invention may be provided with a high-frequency power supply for plasma as described above, a plasma torch having a high-frequency inductive coil, a light-measuring unit for detecting emitted light, and a control unit for analyzing an element by generating a plasma flame using the above-described plasma torch and introducing a sample into the plasma flame.

PREFERRED EMBODIMENT OF THE INVENTION

In the following, a preferred embodiment of the present invention is described in reference to the drawings. Here, the present invention is not limited to the below-described embodiment, but includes various modifications as long as the gist of the present invention is not deviated from.

Figure 1:
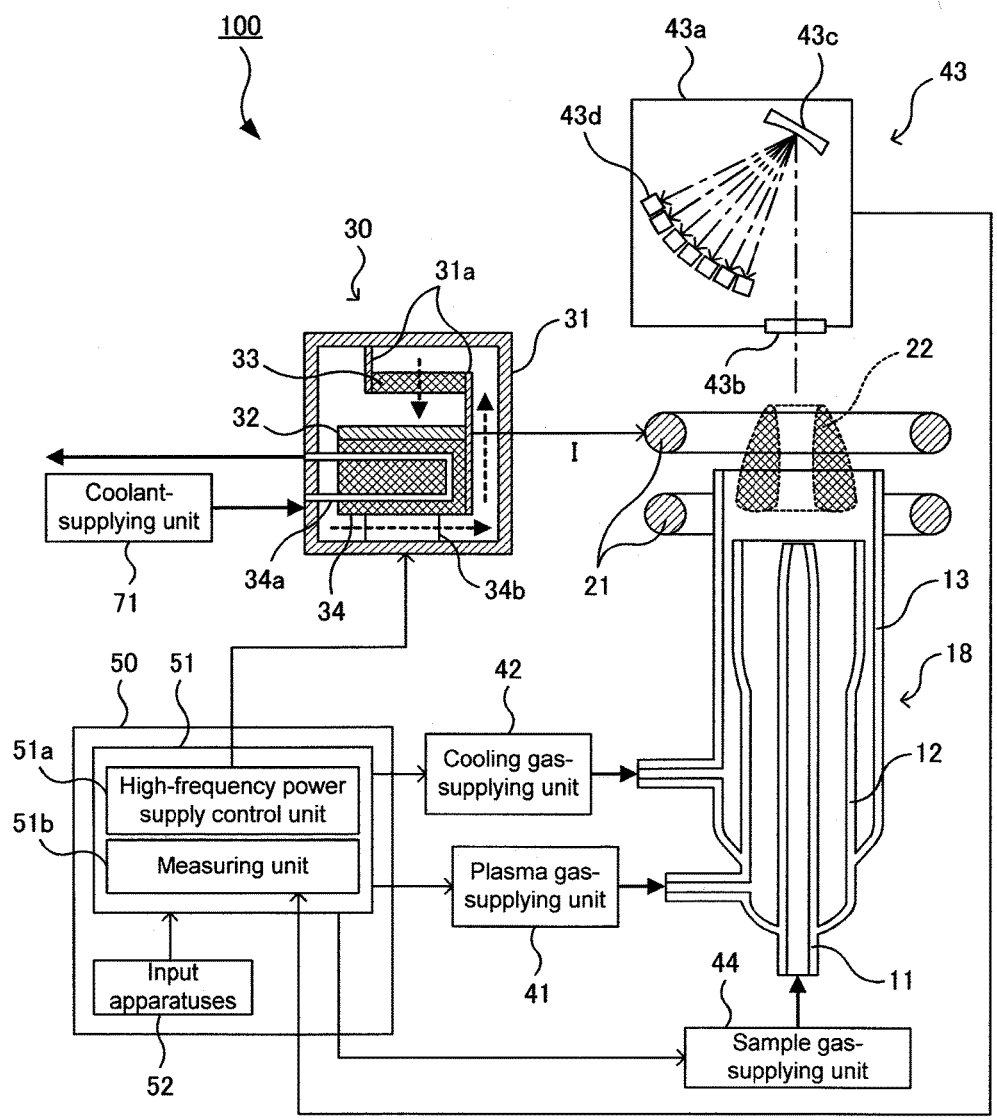
FIG. 1 is a schematic diagram showing the structure of the ICP optical emission spectrometer according to an embodiment.
Figure 2:
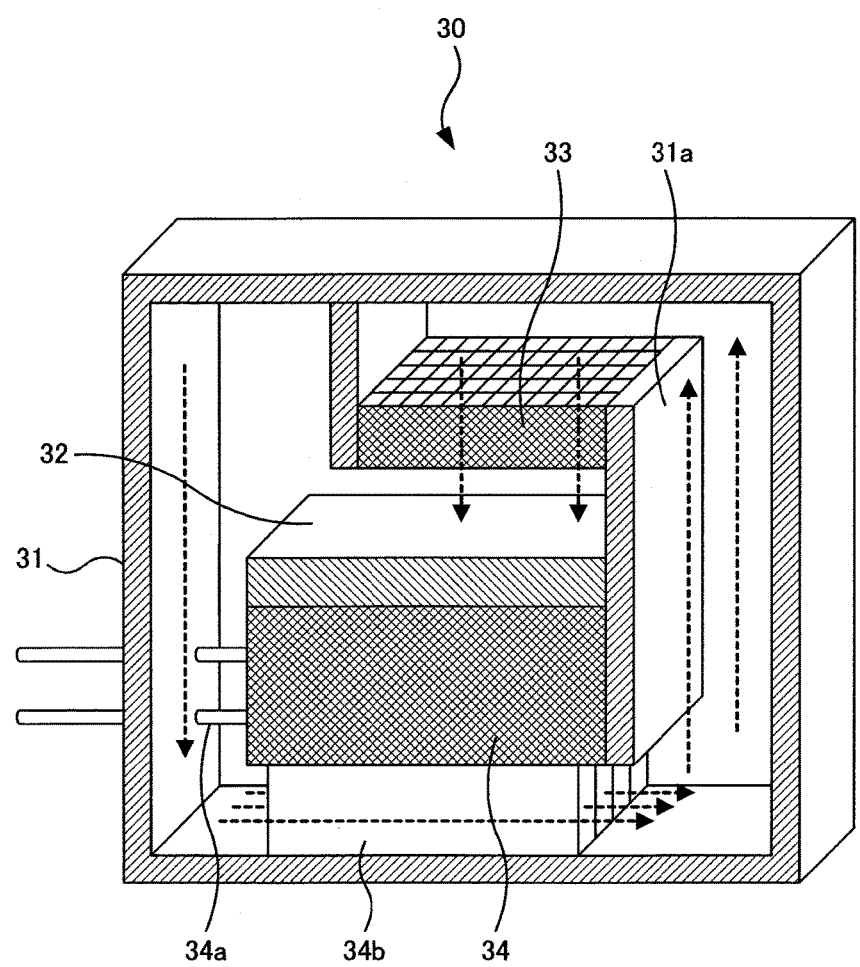
FIG. 2 is a cross-sectional perspective diagram showing the high-frequency power supply for plasma in FIG. 1.

FIG. 1 is a schematic diagram showing the structure of the ICP optical emission spectrometer according to an embodiment. FIG. 2 is a cross-sectional perspective diagram showing the high-frequency power supply for plasma in FIG. 1. Here, the same symbols are attached to the same or similar components as in the ICP optical emission spectrometer 200.

An ICP optical emission spectrometer 100 is provided with a plasma torch 18 for emission spectrometry that generates a plasma flame 22, a sample gas-supplying unit 44, a plasma gas-supplying unit 41, a cooling gas-supplying unit 42, a light-measuring unit 43 for detecting emitted light, a high-frequency power supply 30 for plasma that supplies a high-frequency current I, and a computer (control unit) 50 for controlling the entirety of the ICP optical emission spectrometer 100.

The high-frequency power supply 30 for plasma is provided with a housing 31 closed airtight, a high-frequency circuit substrate 32 placed inside the housing 31, a cooling cover block 34 placed inside the housing 31, a cooling fan 33 placed inside the housing 31, and a coolant-supplying unit 71 placed outside the housing 31.

The housing 31 is in rectangular parallelepiped form (30 cm×30 cm×30 cm, for example) having a space inside, and the inside is closed airtight. That is to say, no dust or the like enters into the housing 31.

Figure 3:
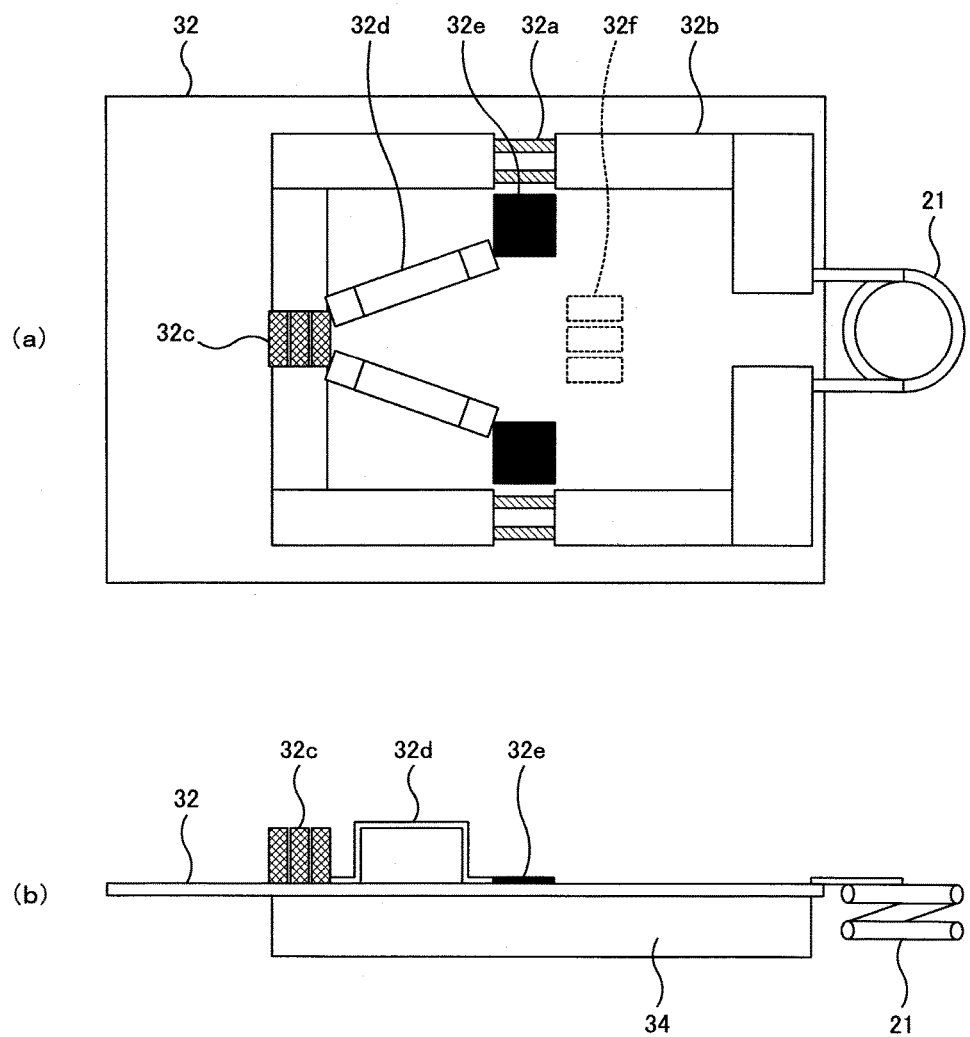
FIGS. 3(a) and 3(b) are a plan diagram and a side diagram showing a high-frequency circuit substrate.

FIG. 3(a) is a plan diagram showing an example of the high-frequency circuit substrate, and FIG. 3(b) is a side diagram showing the example of the high-frequency circuit substrate. The high-frequency circuit substrate 32 is a substrate (27 cm×18 cm×1.6 mm) made of FR4 (Flame Retardant Type 4, thermal conductivity: 0.33 W/mk) in plate form, and power MOSFETs 32e, compact ceramic capacitors 32c, pulse transformers 32a, wires 32b and Ls (inductors) 32d, which are elements for supplying a high-frequency current I to a high-frequency inductive coil 21, are mounted on the upper surface of the substrate, and at the same time, bypass capacitors 32f are mounted on the lower surface of the substrate. In addition, a grease with high heat conduction (thermal conductivity: 2.8 W/mk, made by Shin-Etsu Chemical Co., Ltd.) is applied to the substrate in order to increase the heat conduction to the cooling block. In addition, the high-frequency circuit substrate 32 is placed in the center portion inside the housing 31.

The cooling copper block 34 is a rectangular parallelepiped (15 cm×15 cm×5 cm, for example) where a coolant path 34a for allowing cooling water (coolant) to flow through is formed so as to wind through the inside. The inlet of the flow path and the outlet of the flow path are formed on one side of the coolant copper block 34, and fins 34b are formed on the lower surface. The fins 34b are a number of plate bodies made of aluminum in such a manner that each plate body runs from one side of the cooling copper block 34 to the other side, and the plate bodies are placed so as to be parallel to each other.

In addition, the upper surface of the cooling copper block 34 makes contact with the lower surface of the high-frequency circuit substrate 32 in the arrangement. The thus-formed cooling copper block 34 is cooled when cooling water (5° C. to 31° C., for example) flows through the coolant path 34a, and then the high-frequency circuit substrate 32 is cooled, and as a result, the elements mounted on the high-frequency circuit substrate 32 (power MOSFETs 32e, pulse transformers, 32a, wires 32b, bypass capacitors 32f and compact ceramic capacitors 32c) are cooled.

The cooling fan 33 is provided above the high-frequency circuit substrate 32 so as to face the upper surface of the high-frequency circuit substrate 32 with the absorbing side on the upper side and the exhaust side on the lower side. Thus, the cooling fan 33 allows air to flow from the absorbing side to the exhaust side when rotating. At this time, the cooling fan 33 is in a position so that the wind from the cooling fan 33 directly hits the elements that are inappropriate for cooling through heat conduction, such as the pulse transformers 32a, the Ls (inductors) 32d and the compact ceramic capacitors 32c.

Furthermore, a duct (air path) 31a for supplying the air that has flown through the fins 34b to the absorbing side of the cooling fan 33 is provided inside the housing 31. Concretely, the duct 31a is formed in such a manner that air flows from the left side to the right side beneath the cooling copper block 34, from the lower side to the upper side in the right portion of the housing 31, from the right side to the left side in the upper portion of the housing 31, and passes through the inside of the cooling fan 33, and after that hits the elements on the high-frequency circuit substrate 32 as wind and again flows from the left side to the right side beneath the cooling copper block 34. That is to say, air saturates the housing 31. When air flows from the left side to the right side beneath the cooling copper block 34, it flows through the fan 34b.

The thus-formed cooling fan 33 rotates when the elements on the high-frequency circuit substrate 32 (power MOSFETS 32e, pulse transformers 32a, wires 32b, bypass capacitors 32f, compact ceramic capacitors 32c, Ls (inductors) 32d) supply a high-frequency current I, and thus emit heat. As a result, the cooling fan 33 and the duct 31a allow air to flow through the fins 34b from the left side to the right side of the cooling copper block 34 so as to be cooled so that the thus-cooled air passes through the inside of the cooling fan 33, and after that hits the elements on the high-frequency circuit substrate 32 as a wind to radiate the heat generated in the elements on the high-frequency circuit substrate 32, and again the warmed air flows through the fins 34b from the right side to the left side of the cooling copper block 34 so as to be cooled, and this process is repeated.

The computer (control unit) 50 is a general purpose computer of which the hardware is formed of a CPU 51 and input apparatuses 52, such as a keyboard and a mouse, when shown as blocks for description. In addition, the CPU 51 has a measuring unit 51b for carrying out qualitative analysis and quantitative analysis on the basis of the emission spectrum and a high-frequency power supply control unit 51a when the functions processed by the CPU 51 are divided into blocks for description.

The high-frequency power supply control unit 51a controls the high-frequency circuit substrate 32, the cooling fan 33 and the coolant-supplying unit 71 on the basis of the input signal from the input apparatuses 52, concretely, the high-frequency power supply control unit 51a allows the elements on the high-frequency circuit substrate 32 to supply a high-frequency current I to the high-frequency inductive coil 21, and at the same time allows cooling water to flow through the coolant path 34a in the cooling copper block 34 using the coolant-supplying unit 71 and air to flow through the duct 31a using the cooling fan 33 when an operator inputs an input signal "Turn on plasma" from the input apparatuses 52. In addition, the high-frequency power supply control unit 51a stops the supply of the high-frequency current I from the elements on the high-frequency circuit substrate 32 to the high-frequency inductive coil 21, and at the same time stops the cooling water from flowing through the coolant path 34a in the cooling copper block 34 using the coolant-supplying unit 71 and stops the air from flowing through the duct 31a using the cooling fan 33 when an operator inputs an input signal "Turn off plasma" from the input apparatuses 52.

As described above, the ICP optical emission spectrometer 100 according to the present invention can make it possible to continuously turn on the plasma flame 22 by sufficiently cooling the elements mounted on the high-frequency circuit substrate 32. In addition, the elements on the high-frequency circuit substrate 32 can be prevented from being broken due to the entrance of dust or the like by making the inside of the housing 31 of the high-frequency power supply 30 for plasma be a space sealed airtight.

Another Embodiment

Though the above-described ICP optical emission spectrometer 100 has such a structure that a coolant path 34a for allowing cooling water to flow through is formed so as to wind through the inside of the cooling copper block 34, the structure may have a Peltier element attached to the cooling copper block 34.

EXAMPLES

In the following, the present invention is described in further detail by reference to examples, but the present invention is not limited to these examples.

A heat network of a high-frequency power supply 30 for plasma was fabricated according to an example, and the surface temperature of the elements mounted on the high-frequency circuit substrate 32 were calculated using the following formulas when the flowing current was 20.7 Arms.

Figure 4:
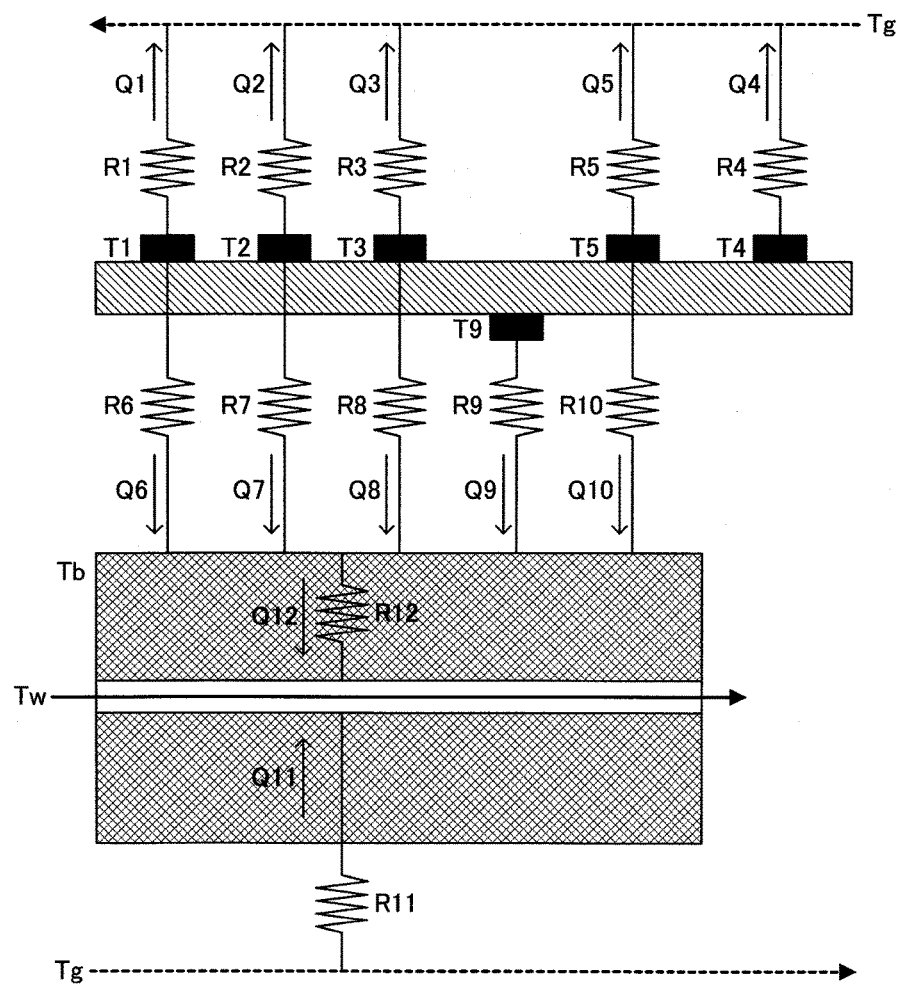
FIG. 4 is a diagram showing a heat network.
Figure 5:
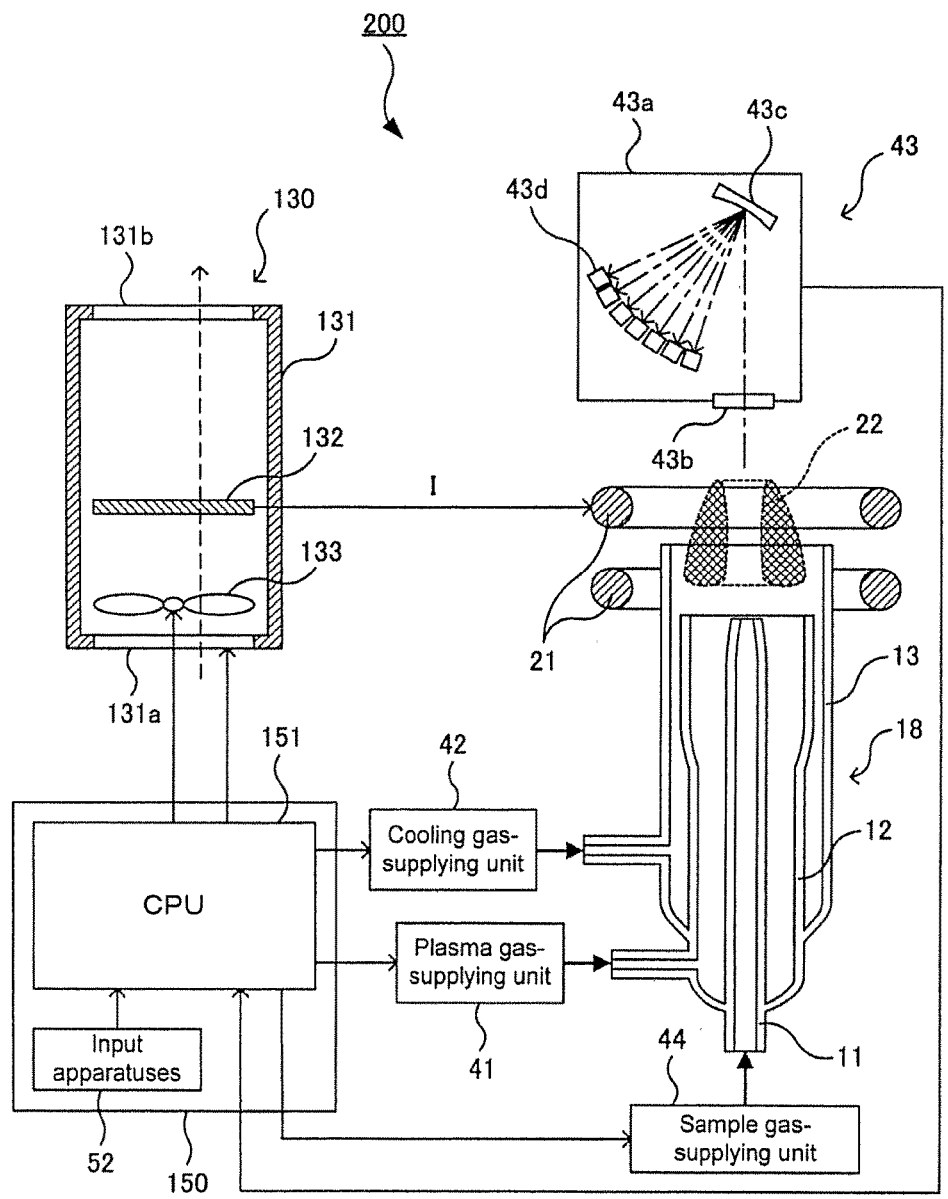
FIG. 5 is a schematic diagram showing the structure of an example of a conventional ICP optical emission spectrometer.

FIG. 4 is a diagram showing a heat network. Here, Tw is the temperature of the cooling water, Tb is the surface temperature of the cooling copper block 34, and Tg is the air temperature. In addition, T1 is the surface temperature of the pulse transformer 32a, T2 is the surface temperature of the wire 32b, T3 is the surface temperature of the compact ceramic capacitor 32c, T9 is the surface temperature of the bypass capacitor 32f, T5 is the surface temperature of the power MOSFET 32e, and T4 is the surface temperature of the L (inductor) 32d. Here, Q is the amount of heat and R is the thermal resistance.

$T1 - Tg = Q1 \times R1$ $T2 - Tg = Q2 \times R2$ $T3 - Tg = Q3 \times R3$ $T4 - Tg = Q4 \times R4$ $T5 - Tg = Q5 \times R5$ $T1 - Tb = Q6 \times R6$ $T2 - Tb = Q7 \times R7$ $T3 - Tb = Q8 \times R8$ $T9 - Tb = Q9 \times R9$ $T5 - Tb = Q10 \times R10$ $Tg - Tw = Q11 \times R11$ $Tb - Tw = Q12 \times R12$ $Q1 + Q6 = 11.2$ $Q2 + Q7 = 5.7$ $Q3 + Q8 = 6$ $Q4 = 4.8$ $Q9 = 4.4$ $Q5 + Q10 = 571$ $Q11 = Q1 + Q2 + Q3 + Q4 + Q5$ $Q12 = 598.3 - Q1 - Q2 - Q3 - Q4 - Q5$ As a result, when the temperature of the cooling water was Tw=31° C., the surface temperature of the pulse transformer 32a was T1=53.2° C., the surface temperature of the wire 32b was T2=52° C., the surface temperature of the compact ceramic capacitor 32c was T3=65° C., the surface temperature of the bypass capacitor 32f was T9=63° C., the surface temperature of the L (inductor) 32d was T4=57° C., the surface temperature of the power MOSFET 32e was T5=78.2° C., the surface temperature of the cooling copper block 34 was Tb=50.8° C., and the air temperature was Tg=35.7° C.

As described above, in the high-frequency power supply 30 for plasma according to the example, the elements mounted on the high-frequency circuit substrate 32 can be sufficiently cooled.

INDUSTRIAL APPLICABILITY

The present invention can be applied to ICP optical emission spectrometers and the like.

EXPLANATION OF SYMBOLS 18 plasma torch for emission spectrometry
21 high-frequency inductive coil
22 plasma flame
30 high-frequency power supply for plasma
31 housing
31a duct (air path)
32 high-frequency circuit substrate
33 cooling fan
34 cooling copper block (cooling block)
34a coolant path
34b fins

What is claimed is:

1. A high-frequency power supply for plasma, comprising:
a housing;
a high-frequency circuit substrate placed inside said housing;
a circuitry element for supplying a high-frequency current to a high-frequency inductive coil, the circuitry element generating heat and being mounted on said high-frequency circuit substrate;
a coolant supplying unit for supplying liquid coolant;
a cooling block having an upper face on which said high-frequency circuit substrate to be cooled is placed and a lower face including fins for allowing the air to flow through so that the air is cooled, the cooling block including a coolant path for allowing the liquid coolant to flow through, the coolant path being disposed inside said cooling block between the upper face and the lower face, and the cooling block being cooled by the liquid coolant; and
a fan for sending air, which has been flown through and cooled by said fins, to the high-frequency circuit substrate, thereby cooling said circuit substrate, wherein:
said housing encloses air-tightly the high-frequency circuit substrate, the circuit element, the cooling block and the fan, and the coolant supplying unit is disposed outside said housing,
an air path is provided in said housing for supplying the air that has flown through said fins provided at the lower face of the cooling block to an intake side of said fan and for blowing the air from said fan to said high-frequency circuit substrate placed on the upper face of the cooling block,
the high-frequency circuit substrate is cooled by the cooling block through which the coolant passes and the fins receives heat from the air thereby cooling the air, the circuitry element includes a power MOSFET, a ceramic capacitor, a pulse transformer, an inductor and a bypass capacitor, and
the power MOSFET, the ceramic capacitor, the pulse transformer, and the inductor are mounted on an upper surface of the high-frequency circuit substrate, and the bypass capacitor is mounted on a lower surface of the high-frequency circuit substrate opposite to the upper surface.

2. The high-frequency power supply for plasma according to claim 1, wherein:
one or more circuit elements of the circuitry element that are required to be cooled not only by means of said cooling block but also by the air are placed in a region on said high-frequency circuit substrate that faces a portion to which said fan exhausts air.

3. The high-frequency power supply for plasma according to claim 2, wherein
the inside of said housing is closed airtight, and
said cooling block, said fan and said air path are provided inside said housing.

4. The high-frequency power supply for plasma according claim 2, wherein said fan is placed above said high-frequency circuit substrate.

5. The high-frequency power supply for plasma according to claim 2, wherein a Peltier element is attached to said cooling block.

6. An ICP optical emission spectrometer, comprising:
the high-frequency power supply for plasma according to claim 2;
a plasma torch having a high-frequency inductive coil;
a light-measuring unit for detecting emitted light; and
a control unit for analyzing an element by generating a plasma flame using said plasma torch and introducing a sample into the plasma flame.

7. The high-frequency power supply for plasma according to claim 1, wherein
the inside of said housing is closed airtight, and
said cooling block, said fan and said air path are provided inside said housing.

8. The high-frequency power supply for plasma according claim 7, wherein said fan is placed above said high-frequency circuit substrate.

9. The high-frequency power supply for plasma according to claim 7, wherein a Peltier element is attached to said cooling block.

10. An ICP optical emission spectrometer, comprising:
the high-frequency power supply for plasma according to claim 7;
a plasma torch having a high-frequency inductive coil;
a light-measuring unit for detecting emitted light; and
a control unit for analyzing an element by generating a plasma flame using said plasma torch and introducing a sample into the plasma flame.

11. The high-frequency power supply for plasma according to claim 1, wherein a Peltier element is attached to said cooling block.

12. An ICP optical emission spectrometer, comprising:
the high-frequency power supply for plasma according to claim 1;
a plasma torch having a high-frequency inductive coil;
a light-measuring unit for detecting emitted light; and
a control unit for analyzing an element by generating a plasma flame using said plasma torch and introducing a sample into the plasma flame.

13. The high-frequency power supply for plasma according to claim 1, wherein the said fan is placed at a different location than said cooling block with respect to said high-frequency circuit substrate.

14. The high-frequency power supply for plasma according to claim 1, wherein the coolant supplying unit supplies water at temperature in a range from 5° C. to 31° C. as the liquid coolant.

15. The high-frequency power supply for plasma according to claim 1, wherein the cooling block is made of copper and the fins are made of aluminum.

16. The high-frequency power supply for plasma according to claim 1, wherein a thermal conductive grease is applied to the high-frequency circuit substrate.

* * * * *